US012622816B2

(12) United States Patent
Kharkar et al.

(10) Patent No.: US 12,622,816 B2
(45) **Date of Patent: *May 12, 2026**

(54) DRESSINGS FOR REDUCED TISSUE INGROWTH

(71) Applicants: Systagenix Wound Management, Limited, West Sussex (GB); KCI Licensing, Inc., San Antonio, TX (US)

(72) Inventors: Prathamesh Madhav Kharkar, San Antonio, TX (US); Kristine M. Kieswetter, San Antonio, TX (US); Alexander Waite, San Antonio, TX (US)

(73) Assignees: Systagenix Wound Management, Limited, Bracknell (GB); KCI Licensing, Inc., San Antonio, TX (US)

( * ) Notice: Subject to any disclaimer, the term of this patent is extended or adjusted under 35 U.S.C. 154(b) by 335 days.

This patent is subject to a terminal disclaimer.

(21) Appl. No.: 18/226,596

(22) Filed: Jul. 26, 2023

(65) Prior Publication Data

US 2023/0363953 A1 Nov. 16, 2023

Related U.S. Application Data

(63) Continuation of application No. 17/269,589, filed as application No. PCT/US2019/038273 on Jun. 20, 2019, now Pat. No. 11,752,039.

(Continued)

(51) Int. Cl.
A61F 13/05 (2024.01)
A61F 13/01 (2024.01)
(Continued)

(52) U.S. Cl.
CPC ........ *A61F 13/05* (2024.01); *A61F 13/01029* (2024.01); *A61L 15/28* (2013.01);
(Continued)

(58) Field of Classification Search
CPC .......... A61F 13/00068; A61F 13/00029; A61F 13/0216; A61M 1/90; A61L 15/28; A61L 15/325; A61L 2300/404; A61L 15/425
(Continued)

(56) References Cited

U.S. PATENT DOCUMENTS

| | | |
|---|---|---|
| 1,355,846 A | 10/1920 | Rannells |
| 2,547,758 A | 4/1951 | Keeling |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Andrew J Mensh

(57) ABSTRACT

Dressings are provided herein having a manifold and a biopolymer layer. The configuration and/or compressibility of the manifold and the biopolymer layer can allow for reduced tissue ingrowth and promote wound healing. Methods of making and using the dressings are also provided herein.

20 Claims, 6 Drawing Sheets

Related U.S. Application Data

(60) Provisional application No. 62/723,837, filed on Aug. 28, 2018.

(51) Int. Cl.

| | | |
|---|---|---|
| *A61L 15/28* | (2006.01) | |
| *A61L 15/32* | (2006.01) | |
| *A61L 15/42* | (2006.01) | |
| *A61M 1/00* | (2006.01) | |

(52) U.S. Cl.
CPC ........... *A61L 15/325* (2013.01); *A61L 15/425* (2013.01); *A61M 1/90* (2021.05); *A61L 2300/404* (2013.01)

(58) Field of Classification Search
USPC ........................................................ 604/543
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,216,651 B2 | 5/2007 | Argenta et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 11,752,039 B2 * | 9/2023 | Kharkar .................. A61M 1/90 | |
| | | | 604/543 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2005/0137512 A1 * | 6/2005 | Campbell ............... A61F 17/00 | |
| | | | 602/41 |
| 2007/0185426 A1 * | 8/2007 | Ambrosio ............... A61L 27/52 | |
| | | | 602/43 |
| 2008/0208171 A1 | 8/2008 | Argenta et al. | |
| 2009/0177133 A1 | 7/2009 | Kieswetter et al. | |
| 2010/0160876 A1 | 6/2010 | Robinson et al. | |
| 2011/0077604 A1 | 3/2011 | Weston | |
| 2011/0091515 A1 | 4/2011 | Zilberman et al. | |
| 2011/0251566 A1 | 10/2011 | Zimnitsky et al. | |

(56) References Cited

U.S. PATENT DOCUMENTS

| | | | |
|---|---|---|---|
| 2011/0275972 A1* | 11/2011 | Rosenberg ........ | A61F 13/00991 602/46 |
| 2012/0107366 A1 | 5/2012 | Kapiamba | |
| 2012/0150078 A1 | 6/2012 | Chen et al. | |
| 2012/0250078 A1* | 10/2012 | Yamada ............. | G03G 15/5087 358/1.15 |
| 2014/0163491 A1 | 6/2014 | Schuessler et al. | |
| 2015/0080788 A1 | 3/2015 | Blott et al. | |
| 2015/0157774 A1* | 6/2015 | Zamierowski .......... | A61M 1/92 604/319 |
| 2015/0320434 A1* | 11/2015 | Ingram .................. | A61B 17/32 606/131 |
| 2016/0038626 A1 | 2/2016 | Locke et al. | |
| 2016/0175156 A1 | 6/2016 | Locke et al. | |
| 2017/0182202 A1 | 6/2017 | Halverson et al. | |
| 2017/0196736 A1 | 7/2017 | Long et al. | |
| 2020/0188550 A1 | 6/2020 | Dagger et al. | |
| 2021/0085819 A1 | 3/2021 | Brewster et al. | |
| 2021/0146000 A1 | 5/2021 | Dagger et al. | |
| 2021/0259890 A1 | 8/2021 | Carty et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2537538 A1 | 12/2012 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 9525846 A1 | 9/1995 |
| WO | 96/05873 A1 | 2/1996 |
| WO | 97/18007 A1 | 5/1997 |
| WO | 99/13793 A1 | 3/1999 |
| WO | 2008/091521 A2 | 7/2008 |
| WO | 2008/104609 A1 | 9/2008 |
| WO | 2009097534 A1 | 8/2009 |
| WO | 2013032745 A1 | 3/2013 |
| WO | 2013078214 A1 | 5/2013 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page. English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous or Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

(56) References Cited

OTHER PUBLICATIONS

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

International Search Report and Written Opinion for Corresponding Application No. PCT/US2019/038273, mailed Oct. 2, 2019.

Office Action for related U.S. Appl. No. 17/269,589, dated Oct. 14, 2022.

Office Action for related U.S. Appl. No. 11/657,887, dated Oct. 1, 2008.

Japanese Notice of Rejection Corresponding to Application No. 2020-524154, mailed Sep. 6, 2022.

Cullen et al. "The role of oxidized regenerated cellulose/collagen in chronic wound repair and its potential mechanism of action", International Journal of Biochemistry & Cell Biology, 34(2002), 1544-1556 (Year: 2002).

ISR & WO for corresponding application PCT/US2018/056914, dated Feb. 4, 2019.

Office Action for related U.S. Appl. No. 16/759,935, dated Sep. 16, 2022.

Japanese Office Action for related application 2023-179285, dated Nov. 12, 2024.

* cited by examiner

DRESSINGS FOR REDUCED TISSUE INGROWTH

RELATED APPLICATION

This application is a continuation of U.S. patent application Ser. No. 17/269,589, filed Feb. 19, 2021, which claims the benefit of U.S. National Stage Entry of PCT/US2019/038273, filed Jun. 20, 2019, which claims the benefit, under 35 U.S.C. § 119(e), of the filing of U.S. Provisional Patent Application Ser. No. 62/723,837, entitled "Dressings For Reduced Tissue Ingrowth," filed Aug. 28, 2018, which is incorporated herein by reference for all purposes.

TECHNICAL FIELD

The invention set forth in the appended claims relates generally to tissue treatment systems and more particularly, but without limitation, to dressings for reduced tissue ingrowth.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," "sub-atmospheric pressure" and "topical negative-pressure," for example. Negative-pressure therapy may provide a number of benefits, including proliferation of dermal, epithelial and subcutaneous tissues, improved interstitial fluid and blood flow, and macroscopic and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for reducing tissue ingrowth in a negative-pressure therapy environment are set forth in the appended claims. Illustrative embodiments are also provided to enable a person skilled in the art to make and use the claimed subject matter.

For example, in some embodiments, dressings are provided that reduce the potential of tissue ingrowth while also addressing challenges to wound healing, such as high levels of matrix metalloproteases (MMPs) and stimulating granulation tissue formation.

More generally, dressings are provided comprising a manifold and a biopolymer layer. In some embodiments, the manifold has a wound facing side, a non-wound facing side opposite the wound facing side, and outer edges between the wound facing and non-wound facing sides; and the biopolymer layer is configured to be in contact with the wound facing side and at least a portion of the outer edges of the manifold, and further configured to reduce or prevent the ingrowth of tissue into said portion of the outer edges during negative pressure wound therapy. Additionally or alternatively, in other example embodiments the biopolymer layer may have a longer length and/or a larger surface area than the manifold.

In further embodiments, dressings are provided having a manifold and a biopolymer layer coupled to the manifold, wherein the manifold has a compressibility index value greater than a dry state compressibility index value of the biopolymer layer, and less than a hydrated state compressibility index value of the biopolymer layer.

Methods of making the dressings are also provided herein, wherein some example embodiments include contacting at least a portion of the manifold with a biopolymer slurry in aqueous base; and freeze drying the manifold and the biopolymer slurry to form a biopolymer layer coupled to the manifold.

Additionally, in other example embodiments, methods of making the dressings further include perforating the manifold or partially cutting the manifold to provide one or more removable parts. This may allow customization of the manifold for end use.

Methods of using the dressings for treating a tissue site with negative pressure wound therapy are also provided herein, wherein some example embodiments include applying a dressing described herein to the surface of a wound; sealing the dressing to epidermis adjacent to the surface wound; fluidly coupling the dressing to a negative pressure source; and applying negative pressure from the negative pressure source to the dressing and promoting healing and tissue granulation.

Additionally, in other example embodiments, the dressings described herein may be used as a secondary wound dressing for treating a tissue site.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
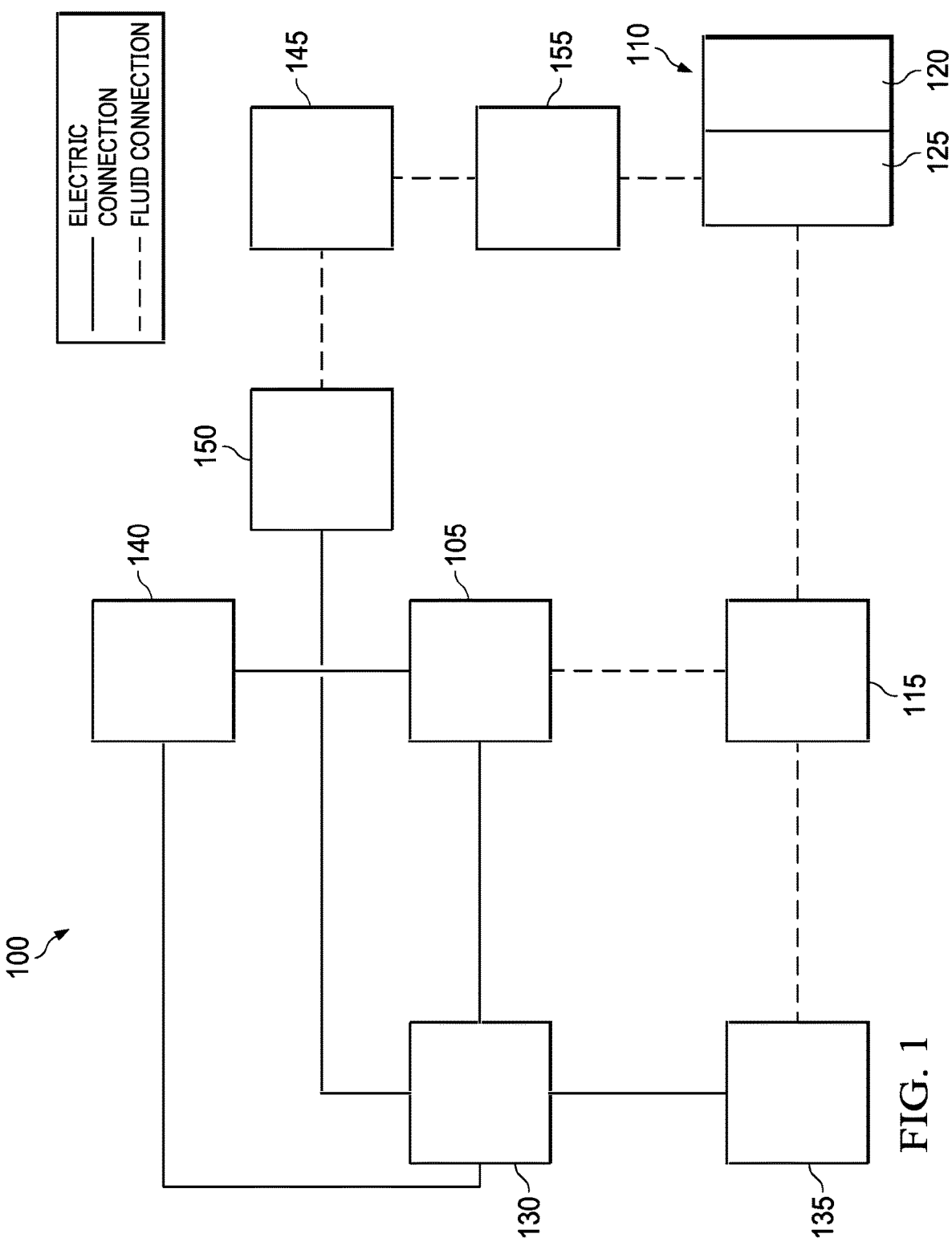
FIG. 1 is a functional block diagram of an example embodiment of a therapy system that can provide negative-pressure treatment and instillation treatment in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may comprise or consist essentially of a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSA-T.R.A.C.™ Pad available from Kinetic Concepts, Inc. of San Antonio, Texas.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

The therapy system 100 may also include a source of instillation solution. For example, a solution source 145 may be fluidly coupled to the dressing 110, as illustrated in the example embodiment of FIG. 1. The solution source 145 may be fluidly coupled to a positive-pressure source such as a positive-pressure source 150, a negative-pressure source such as the negative-pressure source 105, or both in some embodiments. A regulator, such as an instillation regulator 155, may also be fluidly coupled to the solution source 145 and the dressing 110 to ensure proper dosage of instillation solution (e.g. saline) to a tissue site. For example, the instillation regulator 155 may comprise a piston that can be pneumatically actuated by the negative-pressure source 105 to draw instillation solution from the solution source during a negative-pressure interval and to instill the solution to a dressing during a venting interval. Additionally or alternatively, the controller 130 may be coupled to the negative-pressure source 105, the positive-pressure source 150, or both, to control dosage of instillation solution to a tissue site. In some embodiments, the instillation regulator 155 may also be fluidly coupled to the negative-pressure source 105 through the dressing 110, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130, the solution source 145, and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material. In some embodiments, components may be coupled wirelessly.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, absorbent, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

As noted above, a dressing 110 may comprise or consist essentially of a tissue interface 120, a cover 125, or both in some embodiments. The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may comprise or consist essentially of a manifold having a wound facing side, a non-wound facing side opposite the wound facing side, and outer edges between the wound facing and non-wound facing sides. A manifold in this context may comprise or consist essentially of a means for collecting or distributing fluid across the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous materials that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, a manifold suitable for the tissue interface 120 may comprise or consist essentially of open-cell foam having pore sizes and free volume that may vary according to needs of a prescribed therapy. For example, reticulated foam having a free volume of at least 60%, at least 70%, at least 80%, or at least 90% may be suitable for many therapy applications. For example reticulated foam having a free volume of about 60 to about 100 or about 70 to about 90 may be suitable. Additionally, foam having an average pore size in a range of 400-600 microns (40-50 pores per inch) may be particularly suitable for some types of therapy.

In some embodiments, the 25% compression force deflection (CFD) of the manifold can range from about 0.2 psi to about 8.0 psi, preferably from about 0.25 psi to about 0.50 psi and even more preferably from about 2.0 psi to about 2.8 psi in some embodiments. Additionally or alternatively, the 25% CFD of the manifold may be at least 0.35 pounds per square inch, and the 65% CFD may be at least 0.43 pounds per square inch. CFD is a standard compressibility measurement known in the art. For example, see Compression Force Deflection of Flexible Polyurethane Foam per ASTM D3574.

Additionally or alternatively, the compressibility of the manifold can be measured by calculating a compressibility index value. A compressibility index value as used herein represents a % decrease in specimen volume per unit volume per unit load (i.e., 1 kg). Specifically, the compressibility index value can be calculated using a 1 kg load when the specimen is in a dry state or a hydrated state.

To calculate the compressibility index value of the specimen in the dry state, changes in height are measured experimentally before and after addition of 1 kg load. For the dry state, the sample is used as is. For the hydrated state, the sample is submerged into a water sink until complete saturation is achieved and then removed. Excess water is removed, for example, by tapping gently with an absorbent such as tissue paper. An example of a compressibility index value calculation of a manifold is as follows:

Length=60 mm
Width=60 mm
Height=12.73 mm
Height under compression=8.97 mm
Volume (original)=45828 mm$^3$
Volume (after compression)=32292 mm$^3$
% change in volume=compressibility index=29.53%

In some embodiments, the compressibility index value of the manifold in either the dry or hydrated state can be about zero, about 5%, about 10%, about 15%, about 20%, about 25%, about 30%, about 35%, about 40%, about 45% or about 50%. Additionally or alternatively, the compressibility index value of the manifold in either the dry or hydrated state can range from about zero to about 50%, about 5% to about 45%, about 10% to about 40%, about 10% to about 35%, about 15% to about 35% or about 20% to about 35%. In some embodiments, the compressibility index value of the manifold in the dry state and/or the hydrated state may be about 30%.

The tensile strength of the manifold may also vary according to needs of a prescribed therapy. For example, the tensile strength of foam may be increased for instillation of topical treatment solutions. In some embodiments, the tensile strength of the manifold may be at least 10 pounds per square inch. Additionally or alternatively, the manifold may have a tear strength of at least 2.5 pounds per inch.

In some embodiments, the manifold may be foam comprised of polyols such as polyester or polyether, isocyanate such as toluene diisocyanate, and polymerization modifiers such as amines and tin compounds. In some examples, the manifold may be reticulated polyurethane foam such as found in GRANUFOAM™ dressing or V.A.C. VERA-FLO™ dressing, both available from Kinetic Concepts, Inc. of San Antonio, Texas.

The manifold may be either hydrophobic or hydrophilic. In an example in which the manifold may be hydrophilic, the manifold may also wick fluid away from a tissue site, while continuing to distribute negative pressure to the tissue site. The wicking properties of the manifold may draw fluid away from a tissue site by capillary flow or other wicking mechanisms. An example of a hydrophilic material that may be suitable is a polyvinyl alcohol, open-cell foam such as V.A.C. WHITEFOAM™ dressing available from Kinetic Concepts, Inc. of San Antonio, Texas. Other hydrophilic foams may include those made from polyether. Other foams that may exhibit hydrophilic characteristics include hydrophobic foams that have been treated or coated or synthesized with chemistries that have ester linkages instead of ether linkages to provide hydrophilicity.

Additionally or alternatively, the manifold may comprise silicone, polyvinyl alcohol, or a combination of silicone and polyvinyl alcohol.

In some embodiments, the manifold may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The manifold may further serve as a scaffold for new cell-growth, or a scaffold material may be used in conjunction with the manifold to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, keratins, chitosans or processed allograft materials.

The thickness of the manifold may also vary according to needs of a prescribed therapy. For example, the thickness of the manifold may be decreased to reduce tension on peripheral tissue. The thickness of the manifold can also affect the conformability of the manifold. In some embodiments, a thickness in a range of about 5 millimeters to 30 millimeters, or about 5 millimeters to about 10 millimeters may be suitable.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or consist of, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minnesota; polyurethane (PU) drape, commercially available from Avery Dennison Corporation, Pasadena, California; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 125 may comprise INSPIRE 2301 having an MVTR (upright cup technique) of 2600 g/m$^2$/24 hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 145 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in container 115.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

Figure 2:
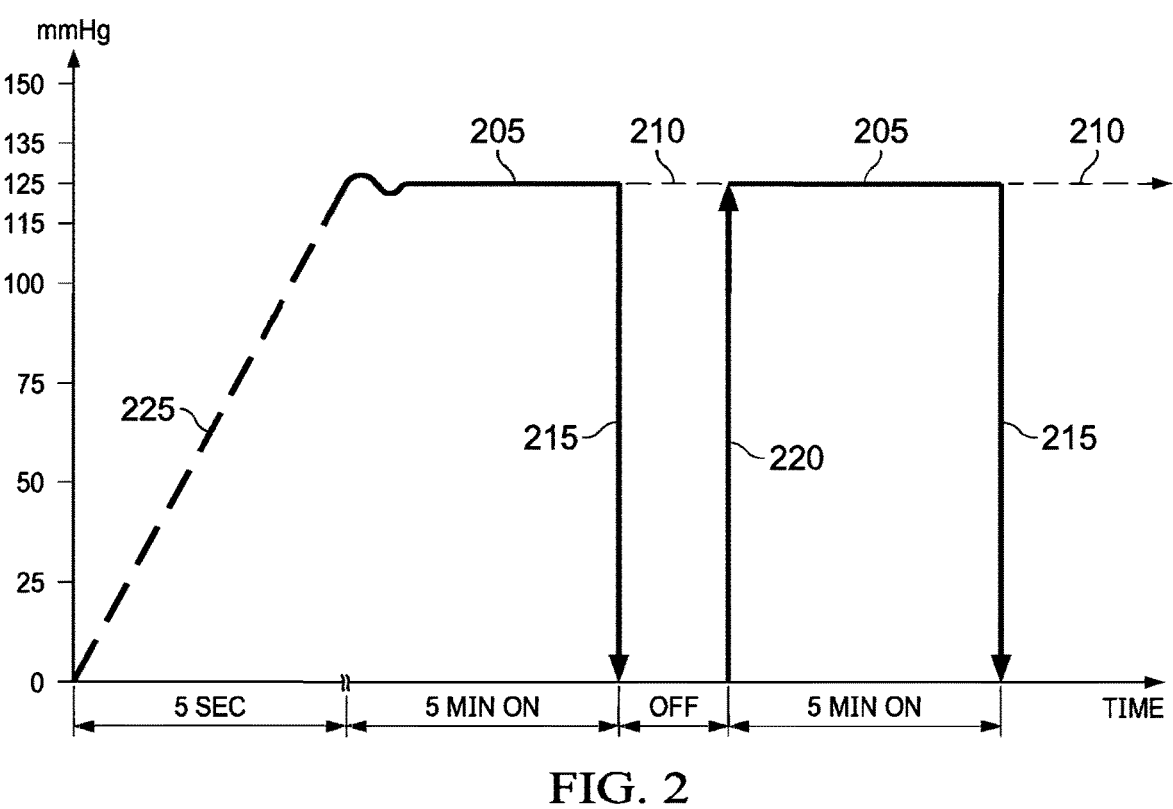
FIG. 2 is a graph illustrating additional details of example pressure control modes that may be associated with some embodiments of the therapy system of FIG. 1.

FIG. 2 is a graph illustrating additional details of an example control mode that may be associated with some embodiments of the controller 130. In some embodiments, the controller 130 may have a continuous pressure mode, in which the negative-pressure source 105 is operated to provide a constant target negative pressure, as indicated by line 205 and line 210, for the duration of treatment or until manually deactivated. Additionally or alternatively, the controller may have an intermittent pressure mode, as illustrated in the example of FIG. 2. In FIG. 2, the x-axis represents time and the y-axis represents negative pressure generated by the negative-pressure source 105 over time. In the example of FIG. 2, the controller 130 can operate the negative-pressure source 105 to cycle between a target pressure and atmospheric pressure. For example, the target pressure may be set at a value of 125 mmHg, as indicated by line 205, for a specified period of time (e.g., 5 min), followed by a specified period of time (e.g., 2 min) of deactivation, as indicated by the gap between the solid lines 215 and 220. The cycle can be repeated by activating the negative-pressure source 105, as indicated by line 220, which can form a square wave pattern between the target pressure and atmospheric pressure.

In some example embodiments, the increase in negative-pressure from ambient pressure to the target pressure may not be instantaneous. For example, the negative-pressure source 105 and the dressing 110 may have an initial rise time, as indicated by the dashed line 225. The initial rise time may vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time, as indicated by the solid line 220, may be a value substantially equal to the initial rise time as indicated by the dashed line 225.

Figure 3:
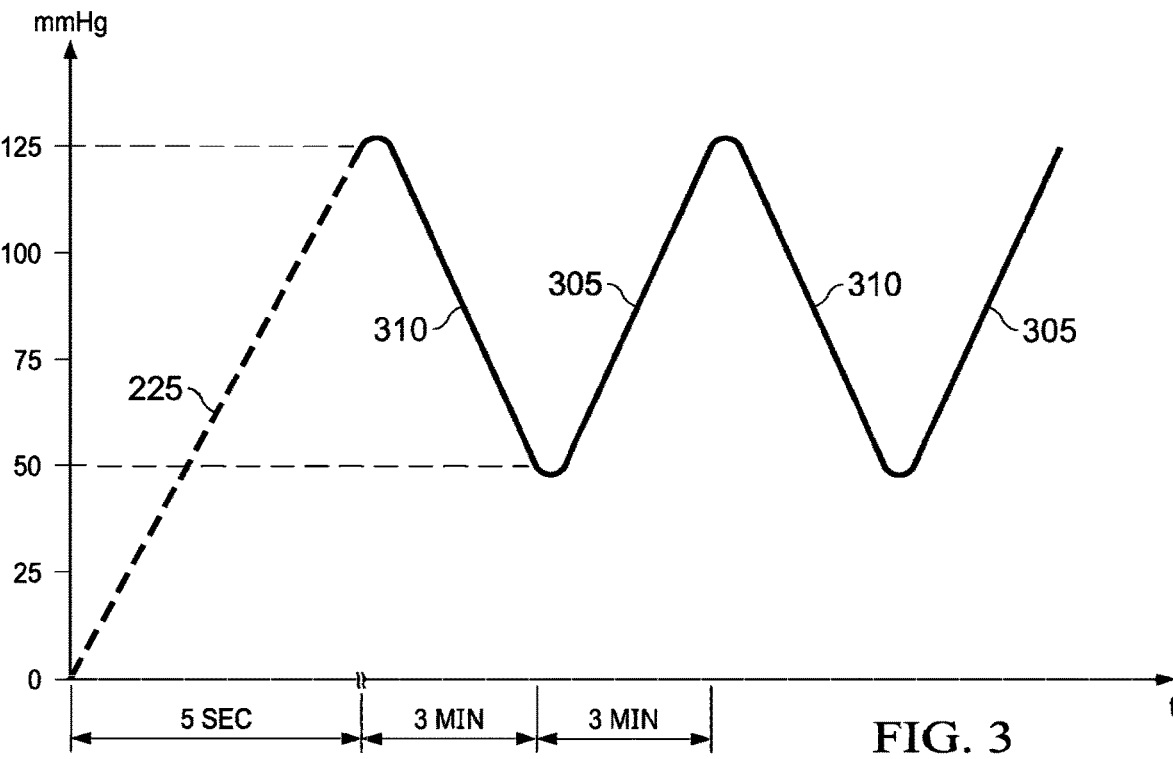
FIG. 3 is a graph illustrating additional details that may be associated with another example pressure control mode in some embodiments of the therapy system of FIG. 1.

FIG. 3 is a graph illustrating additional details that may be associated with another example pressure control mode in some embodiments of the therapy system 100. In FIG. 3, the x-axis represents time and the y-axis represents negative pressure generated by the negative-pressure source 105. The target pressure in the example of FIG. 3 can vary with time in a dynamic pressure mode. For example, the target pressure may vary in the form of a triangular waveform, varying between a negative pressure of 50 and 125 mmHg with a rise time 305 set at a rate of +25 mmHg/min. and a descent time 310 set at −25 mmHg/min. In other embodiments of the therapy system 100, the triangular waveform may vary between negative pressure of 50 and 125 mmHg with a rise time 305 set at a rate of +30 mmHg/min and a descent time 310 set at −30 mmHg/min.

In some embodiments, the controller 130 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 130, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

Figure 4:
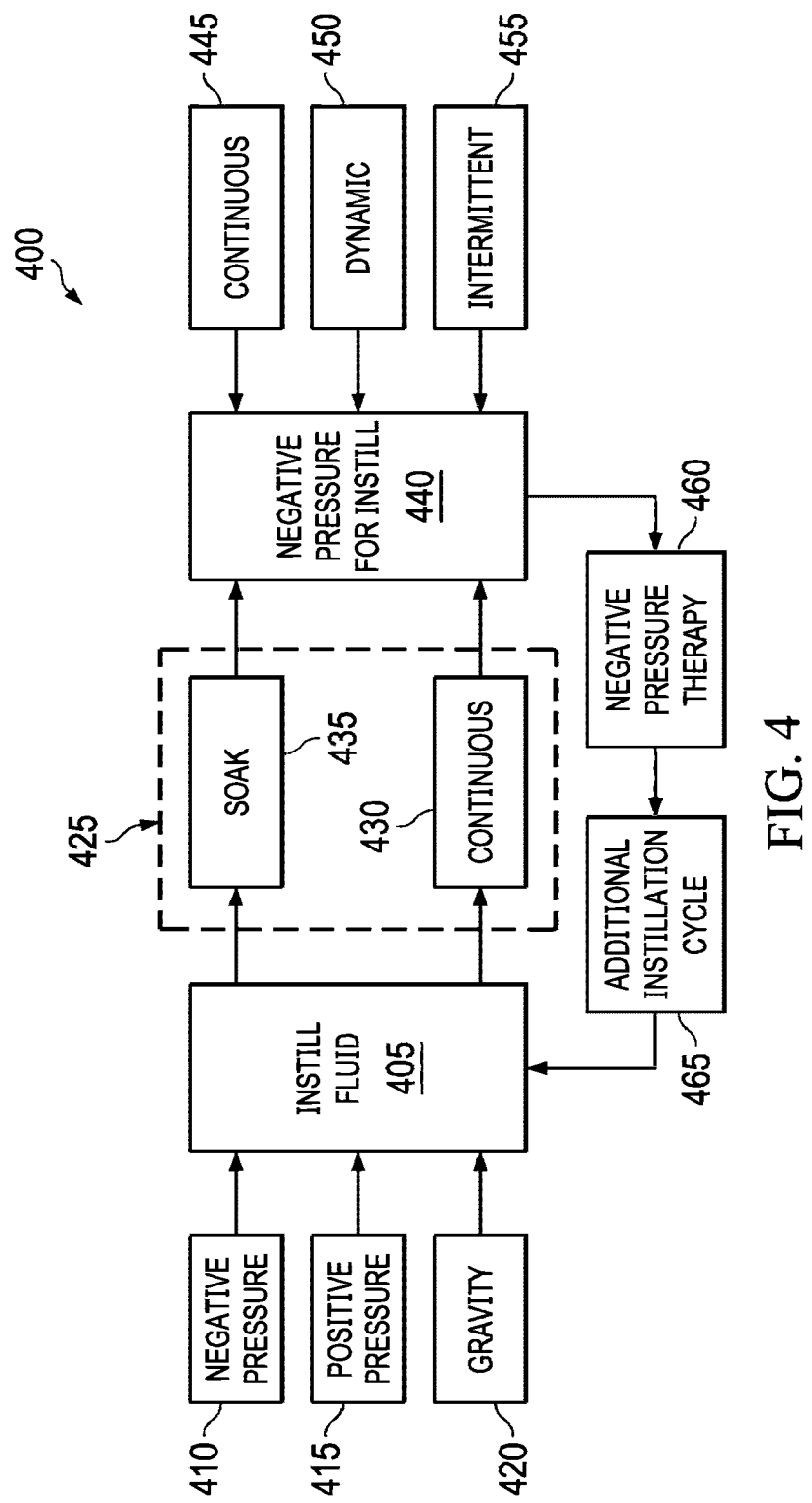
FIG. 4 is a chart illustrating details that may be associated with an example method of operating the therapy system of FIG. 1.

FIG. 4 is a chart illustrating details that may be associated with an example method 400 of operating the therapy system 100 to provide negative-pressure treatment and instillation treatment to the tissue interface 120. In some embodiments, the controller 130 may receive and process data, such as data related to instillation solution provided to the tissue interface 120. Such data may include the type of instillation solution prescribed by a clinician, the volume of fluid or solution to be instilled to a tissue site ("fill volume"), and the amount of time prescribed for leaving solution at a tissue site ("dwell time") before applying a negative pressure to the tissue site. The fill volume may be, for example, between 10 and 500 mL, and the dwell time may be between one second to 30 minutes. The controller 130 may also control the operation of one or more components of the therapy system 100 to instill solution, as indicated at 405. For example, the controller 130 may manage fluid distributed from the solution source 145 to the tissue interface 120. In some embodiments, fluid may be instilled to a tissue site by applying a negative pressure from the negative-pressure source 105 to reduce the pressure at the tissue site, drawing solution into the tissue interface 120, as indicated at 410. In some embodiments, solution may be instilled to a tissue site by applying a positive pressure from the positive-pressure source 160 to move solution from the solution source 145 to the tissue interface 120, as indicated at 415. Additionally or alternatively, the solution source 145 may be elevated to a height sufficient to allow gravity to move solution into the tissue interface 120, as indicated at 420.

The controller 130 may also control the fluid dynamics of instillation at 425 by providing a continuous flow of solution at 430 or an intermittent flow of solution at 435. Negative pressure may be applied to provide either continuous flow or intermittent flow of solution at 440. The application of negative pressure may be implemented to provide a continuous pressure mode of operation at 445 to achieve a continuous flow rate of instillation solution through the tissue interface 120, or it may be implemented to provide a dynamic pressure mode of operation at 450 to vary the flow rate of instillation solution through the tissue interface 120. Alternatively, the application of negative pressure may be implemented to provide an intermittent mode of operation at 455 to allow instillation solution to dwell at the tissue interface 120. In an intermittent mode, a specific fill volume and dwell time may be provided depending, for example, on the type of tissue site being treated and the type of dressing being utilized. After or during instillation of solution, negative-pressure treatment may be applied at 460. The controller 130 may be utilized to select a mode of operation and the duration of the negative pressure treatment before commencing another instillation cycle at 465 by instilling more solution at 405.

In addition to negative pressure wound therapy, the tissue interface 120 described herein can also be used as secondary wound dressing for treating a tissue site.

Figures 5A, 5B, 5C:
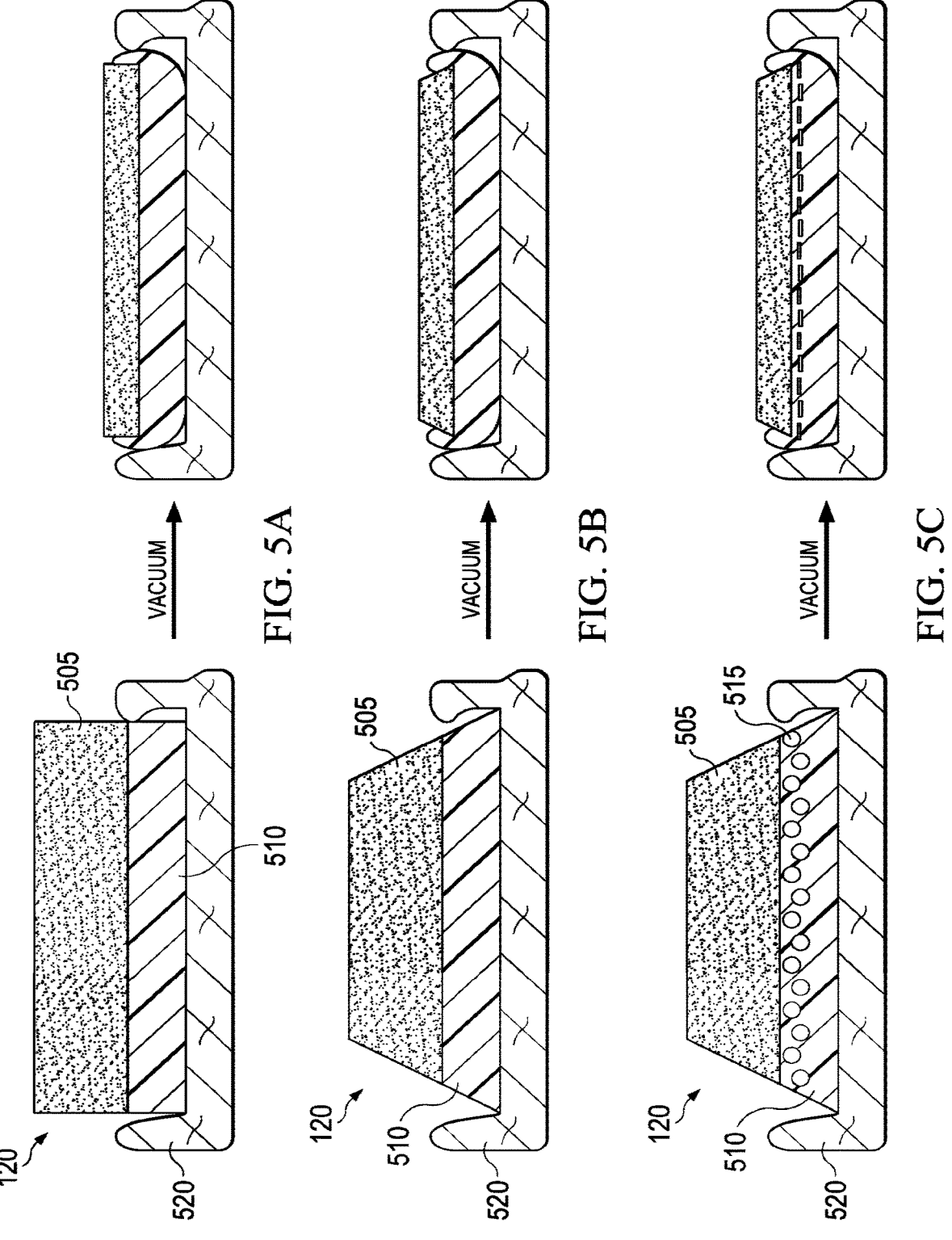
FIGS. 5A-5C are schematic diagrams illustrating additional details of an example of a tissue interface that may be associated with some embodiments of the therapy system of FIG. 1.

As noted above, a dressing described herein may comprise a tissue interface 120. A tissue interface 120 may comprise a manifold 505 and a biopolymer layer 510. In some embodiments, the biopolymer layer 510 is coupled to the manifold. FIGS. 5A-5C are schematic diagrams illustrating additional details that may be associated with some example embodiments of the tissue interface 120. In some embodiments, the tissue interface 120 may comprise more than one component or layer, such as the bi-layer wound insert of FIG. 5A and FIG. 5B. As illustrated in the examples of FIG. 5A and FIG. 5B, the tissue interface 120 may include a manifold 505 and a biopolymer layer 510, which can also be referred to as a base biopolymer layer 510, coupled to the manifold 505. The biopolymer layer 510 may be in direct contact or indirect contact with the manifold 505. In some embodiments, the biopolymer layer 510 is separable from the manifold 505.

In some embodiments, the biopolymer layer 510 may comprise a biological material selected from the group consisting of heparin, collagen, gelatin, hyaluronic acid, chitosan, cellulose, a cellulose derivative, alginate, fibrin, silk, carrageenan, chondroitin sulfate, agarose, keratin, dextran, keratan sulfate, heparan sulfate, fibronectin, laminin, and a combination thereof.

In particular embodiments, the biopolymer layer 510 comprises collagen. Examples of suitable collagens include, but are not limited to native collagens, such as Types I, II and/or III native collagens, atelopeptide collagens, partially hydrolyzed collagens, such as gelatin, regenerated collagen and combinations thereof. The collagen may be present in any suitable amount, e.g., based on total weight of the biopolymer 510, collagen may be present in an amount ≥ about 25 wt %, ≥ about 30 wt %, ≥ about 35 wt %, ≥ about 40 wt %, ≥ about 45 wt %, ≥ about 50 wt %, ≥ about 55 wt %, ≥ about 60 wt %, ≥ about 65 wt %, ≥ about 70 wt %, ≥ about 75 wt %, or ≥ about 80 wt %. Additionally or alternatively, collagen may present, based on total weight of the biopolymer 510, in amount of about 25 wt % to about 80 wt %, about 35 wt % to about 75 wt %, about 40 wt % to about 70 wt %, about 45 wt % to about 65 wt %, or about 50 wt % to about 60 wt %.

13

In some embodiments, the biopolymer 510 may further comprise an anionic polysaccharide. The anionic polysaccharide may be substantially insoluble in water at pH 7. Additionally or alternatively, the anionic polysaccharide may have a molecular weight greater than about 20,000, more preferably greater than about 50,000. The anionic polysaccharide may be in the form of a film, or fibers having a length greater than 1 mm.

Suitable anionic polysaccharides include, but are not limited to, polycarboxylates, alginates, hyaluronates, pectins, carrageenans, xanthan gums, sulfated dextrans, cellulose derivatives, such as carboxymethyl celluloses, and oxidized celluloses. The term "oxidized cellulose" refers to any material produced by the oxidation of cellulose, for example with dinitrogen tetroxide. Such oxidation converts primary alcohol groups on the saccharide residues to carboxylic acid groups, forming uronic acid residues within the cellulose chain. The oxidation generally does not proceed with complete selectivity, and as a result hydroxyl groups on carbons 2 and 3 are occasionally converted to the keto form. These keto units introduce an alkali-labile link, which at pH 7 or higher initiates the decomposition of the polymer via formation of a lactone and sugar ring cleavage. As a result, oxidized cellulose is biodegradable and resorbable or bioresorbable under physiological conditions. Thus, in various aspects, the biopolymer described herein may be resorbable or bioresorbable. As used herein, the terms "resorbable" or "bioresorbable" are synonymous and refer to the ability of at least a portion of a material to disintegrate, degrade, or dissolve upon exposure to physiological fluids or processes such that at least a portion of the material may be absorbed or assimilated, for example, at a tissue site or in vivo in a mammalian body. Resorbability or bioresorbability may be exhibited as a result of a chemical process or condition, a physical process or condition, or combinations thereof.

In some embodiments, oxidized cellulose present in the biopolymer layer 510 may be oxidized regenerated cellulose (ORC), which may be prepared by oxidation of a regenerated cellulose, such as rayon. It has been known that ORC has haemostatic properties. ORC has been available as a haemostatic fabric called SURGICEL® (Johnson & Johnson Medical, Inc.) since 1950. This product may be produced by the oxidation of a knitted rayon material.

The anionic polysaccharide (e.g., ORC) may be present in the biopolymer layer 510 in any suitable amount, e.g., based on total weight of the biopolymer layer 510, an anionic polysaccharide (e.g., ORC) may be present in an amount ≥ about 15 wt %, ≥ about 20 wt %, ≥ about 25 wt %, ≥ about 30 wt %, ≥ about 35 wt %, ≥ about 40 wt %, ≥ about 45 wt %, ≥ about 50 wt %, ≥ about 55 wt %, ≥ about 60 wt %, ≥ about 65 wt %, or ≥ about 70 wt %. Additionally or alternatively, an anionic polysaccharide (e.g., ORC) may be present in the biopolymer layer 510, based on total weight of the biopolymer layer 510, in amount of about 15 wt % to about 70 wt %, about 20 wt % to about 65 wt %, about 25 wt % to about 65 wt %, about 30 wt % to about 60 wt %, about 35 wt % to about 55 wt %, or about 40 wt % to about 50 wt %.

In some embodiments, the biopolymer layer 510 may comprise collagen and an anionic polysaccharide, such as ORC. For example, the biopolymer layer 510 may comprise a lower density combination of collagen and ORC, of about 0.01 g/cm³, found in PROMOGRAN™ Matrix Wound Dressing (available from Acelity L. P. Inc. of San Antonio, Texas). Alternatively, the biopolymer layer 510 may comprise a higher density combination of collagen and an anioinic polysaccharide, such as ORC, of about 0.02 g/cm³,

14 about 0.03 g/cm³, about 0.04 g/cm³, about 0.05 g/cm³, about 0.06 g/cm³, about 0.7 g/cm³, particularly about 0.4 g/cm³. In some embodiments, the higher density combination of collagen and an anionic polysaccharide, such as ORC, can range from about 0.02 g/cm³ to about 0.07 g/cm³ or about 0.03 g/cm³ to about 0.06 g/cm³.

Additionally or alternatively, the biopolymer layer 510 may further comprise an antimicrobial agent. Examples of suitable antimicrobial agents present in the biopolymer layer include, but are not limited to, organic acids such as carboxylic acids, silver, gold, zinc, copper, polyhexamethylene biguanide (PHMB), iodine and combinations thereof. Exemplary carboxylic acids include, but are not limited to ascorbic acid (e.g., (R)-3,4-dihydroxy-5-((S)-1,2-dihydroxyethyl) furan-2(5H)-one or Vitamin C), formic acid, gluconic acid, lactic acid, oxalic acid, tartaric acid, peroxy-pyruvic acid, and combinations thereof. Examples of carboxylic acids include, but are not limited, to citric acid and acetic acid (i.e., ethanoic acid). In some embodiments, the antimicrobial agent present in the biopolymer layer 510 may be citric acid. The antimicrobial agent (e.g., citric acid) may be present in the biopolymer layer 510 in a suitable concentration, e.g., a concentration sufficient to reduce bacteria concentration in a wound, including reducing bacterial biofilms, in order to promote wound healing and/or control infection.

In various aspects, the antimicrobial agent, such as citric acid, may be present in a concentration ≥ about 15 mM, ≥ about 20 mM, ≥ about 25 mM, ≥ about 50 mM, ≥ about 75 mM, ≥ about 100 mM, ≥ about 125 mM, ≥ about 150 mM, ≥ about 175 mM, ≥ about 200 mM, ≥ about 225 mM, ≥ about 250 mM, ≥ about 275 mM, ≥ about 300 mM, ≥ about 325 mM, ≥ about 350 mM, ≥ about 375 mM, ≥ about 400 mM, ≥ about 425 mM, ≥ about 450 mM, ≥ about 475 mM, ≥ about 500 mM, ≥ about 525 mM, ≥ about 550 mM, ≥ about 575 mM, ≥ about 600 mM, ≥ about 650 mM, ≥ about 700 mM, ≥ about 750 mM, ≥ about 800 mM, ≥ about 850 mM, ≥ about 900 mM, ≥ about 950 mM, ≥ about 1M, or ≥ about 2M. In some embodiments, the antimicrobial agent may be present in a concentration ≥ about 200 mM. Additionally or alternatively, the antimicrobial agent may be present in a concentration about 15 mM to about 650 mM, about 20 mM to about 500 mM, about 20 mM to about 400 mM, about 50 mM to about 650 mM, about 50 mM to about 500 mM, about 50 mM to about 400 mM, about 75 mM to about 650 mM, about 75 mM to about 500 mM, about 75 mM to about 400 mM, about 100 mM to about 650 mM, about 100 mM to about 500 mM, or about 100 mM to about 400 mM.

In some embodiments, the biopolymer layer 510 may comprise a metal, for example silver, which may be used as a further antimicrobial agent. The metal may be present in metallic form, in ionic form (e.g., a silver salt), or both. In some embodiments, silver may be present in combination with one or more additional metals, for example, gold, platinum, ferro-manganese, copper, zinc, or a combination thereof. The metal, particularly, silver, may confer antimicrobial properties to the biopolymer layer 510 and in sufficiently lower concentrations, e.g., about 0.10 wt % to about 3.0 wt %, the silver may not cause cytotoxicity in a wound or at a tissue site.

In some embodiments, at least a portion of the metal may be present as a complex of the anionic polysaccharide and the metal, for example, as an ORC-silver complex. As used herein, the term "complex" refers to an intimate mixture at the molecular scale, preferably with ionic or covalent bonding between the metal (e.g., silver) and the polysaccharide (e.g., ORC). The complex may comprise a salt formed between the anionic polysaccharide and Ag+, but it may also comprise silver clusters and/or colloidal silver metal, for example produced by exposure of the complex to light. For example, an anionic polysaccharide (e.g., ORC) may be treated with a silver salt solution to produce a complex of the anionic polysaccharide (e.g., ORC) with silver. The silver salt solution may be an aqueous solution and the solution may be prepared in a quantity sufficient to provide the desired silver concentration in the resultant complex. In some embodiments, the amount of silver in the complex may be from about 0.1% to about 50% by weight based on the weight of the anionic polysaccharide, particularly, from about 1% to about 40%, about 2% to about 30% by weight, and about 5% to about 25%.

In some embodiments, an anionic polysaccharide-metal complex (e.g., ORC-silver complex) may be present in the biopolymer layer 510 in an amount ≥ about 0.10 wt %, ≥ about 0.50 wt %, ≥ about 1.0 wt %, ≥ about 2.0 wt %, ≥ about 3.0 wt %, ≥ about 4.0 wt %, ≥ about 5.0 wt %, ≥ about 6.0 wt %, ≥ about 8.0 wt %, or ≥ about 10 wt %. Additionally or alternatively, an anionic polysaccharide-metal complex (e.g., ORC-silver complex) may be present in the biopolymer 510, based on total weight of the biopolymer 510, in amount of about 0.10 wt % to about 10 wt %, about 0.10 wt % to about 8.0 wt %, about 0.10 wt % to about 5.0 wt %, about 0.50 wt % to about 4.0 wt %, about 0.50 wt % to about 3.0 wt %, or about 0.50 wt % to about 2.0 wt %.

In some embodiments, the biopolymer layer 510 comprises collagen, an anionic polysaccharide (e.g., ORC), and a metal (e.g., silver). For example, the biopolymer layer 510 may comprise PROMOGRAN PRISMA™ Matrix (available from Acelity L.P. Inc of San Antonio, Texas) and, optionally, an antimicrobial agent (e.g., citric acid).

Additionally or alternatively, the biopolymer layer 510 may comprise a synthetic polymer selected from the group consisting of polycaprolactone, polylactic acid, polyglycolic acid, polydioxanone, poly(lactic-co-glycolic acid), polyhydroxybutyrate, polyhydroxyvalerate and a combination thereof. In some embodiments, the synthetic polymer may have a degradation rate that will allow for separation from the manifold 505 in a 7-10 day timeframe.

In some embodiments, the biopolymer layer 510 has a thickness of about 0.1 cm to about 5 cm, preferably about 0.5 cm to about 3 cm.

In some embodiments, the biopolymer layer 510 is configured to be in contact with the wound facing and non-wound facing side and at least a portion of the outer edges of the manifold 505. The biopolymer layer 510 can be configured to reduce or prevent the ingrowth of tissue into at least a portion of the outer edges of the manifold 505, for example, during wound therapy such as negative pressure wound therapy. In some embodiments, the biopolymer layer 510 can be configured to cover or be in contact will the entire surface area of the outer edges of the manifold 505. Additionally, in some embodiments, the biopolymer layer 510 is configured to contact at least a portion (or all) of the outer edges of the manifold 505 only during wound therapy use, such as negative pressure wound therapy use.

The shape and/or size of the manifold 505 and biopolymer layer 510 can be altered such that the biopolymer layer 510 collapses onto the edges of the manifold 505 under application of negative pressure, reducing the exposed surface area for any granulation tissue entrapment. For example, in some embodiments, the manifold 505 and the biopolymer layer 510 together can have a trapezoidal cross-section having an inclined angle from about 20 to about 85 degrees, preferably about 30 to about 45 degrees as shown in the examples of FIGS. 5B and 5C. The inclined cut can be made by any suitable cutting means, for example a rotary cutter, wire cutter, clicker press, and/or laser cutter. The inclined cut can also be further tuned by an end user at the time of use by means of scissors and/or surgical scalpels. Additionally or alternatively, the biopolymer layer 510 may have a longer length than the manifold 505 and/or a larger surface area than the manifold 505. For example, in some embodiments the tissue interface 120 can be manufactured such that the manifold 505 is in contact with the biopolymer layer 510 for only a portion of the biopolymer layer 510 surface area. For instance, when viewed from above, an 8 cm×8 cm area of manifold 505 (e.g. polyurethane foam) may be about center on a 10 cm×10 cm biopolymer layer 510. In some embodiments, an area of overlap between the manifold 505 and the biopolymer layer 510 is about 0.01 cm to about 5 cm, more preferably 0.1 cm to about 3 cm, and most preferably about 0.3 cm to about 1 cm.

In some embodiments, the biopolymer layer 510 can be configured as a wound contact layer to be in direct contact with a wound. As shown in the examples of FIGS. 5A-5C, the biopolymer layer 510 is in direct contact with tissue 520.

In some embodiments, the biopolymer layer 510 is present as a coating on at least one face of the manifold 505. Additionally or alternatively, the biopolymer layer 510 can substantially cover or be co-extensive with at least one face of the manifold 505 and cover one or more edges of the manifold 505 partially or completely.

In some embodiments, the biopolymer layer 510 may have a dry state compressibility index value, as calculated above, of about zero, about 1%, about 2%, about 3%, about 4%, about 5%, about 6%, about 7%, about 8%, about 9%, about 10%, about 15%, about 20%, about 25%, about 30% or about 35%. Additionally or alternatively, the biopolymer layer 510 may have a dry state compressibility index value of about zero to about 35%, or about 1% to about 30%, or about 1% to about 25%, or about 1% to about 20%, or about 2% to about 20%, or about 2% to about 15%, or about 3% to about 10%. In particular embodiments, the dry state compressibility index value of the biopolymer layer 510 may be about 7%.

Additionally or alternatively, the biopolymer layer 510 may have a hydrated stated compressibility index value, as calculated above, of about 60%, about 65%, about 70%, about 75%, about 80%, about 85% or about 90%. Additionally or alternatively, the biopolymer layer 510 may have a hydrated state compressibility index value of about 65% to about 90%, or about 65% to about 85%, or about 65% to about 80%. In particular embodiments, the hydrated state compressibility index value of the biopolymer layer 510 may be about 73%.

In some embodiments, the manifold 505 may have a different compressibility than the biopolymer 510. For example, a dressing provided herein may have a manifold 505 and a biopolymer layer 510 coupled to the manifold 505, wherein the manifold 505 can have a compressibility index value (in either the dry or hydrated state) greater than the dry state compressibility index value of the biopolymer layer 510. Additionally or alternatively, the manifold 505 can also have a lower compressibility index value (in either the dry or hydrated state) than the hydrated state compressibility index value of the biopolymer layer 510.

In some embodiments, the manifold 505 may have a greater compressibility index value (in either the dry or hydrated state) than the dry state compressibility index value of the biopolymer layer 510, such as 10%, 15%, 20%, 25% or even 30% greater than the dry state compressibility index value of the biopolymer layer 510. Alternatively, it may be stated that the biopolymer layer 510 has a lower dry state compressibility index value than the compressibility index value of the manifold 505 in either the dry or hydrated state. For example, the dry state compressibility index of the biopolymer layer 510 may be 10%, 15%, 20%, 25% or even 30% lower than the compressibility index value of the manifold 505 in either the dry or hydrated state.

Without being bound by theory, in some embodiments the compressibility differences between the manifold 505 and the biopolymer layer 510 may allow differential volume change as a response to externally applied subatmospheric pressure. The uneven changes in volume may result in minimal edge area of exposed manifold 505 (e.g. polyurethane foam), whereas the height (and thus the edge area) of the biopolymer layer 510 remains relatively unchanged as shown in the examples of FIGS. 5A-5C. The difference in compressibility between the manifold 505 and the biopolymer layer 510 may minimize the exposed area around the edges of the manifold 505 resulting in minimal to no granulation tissue ingrowth and/or entrapment within the edges of the manifold 505. The minimal edges of exposed manifold 505 may limit potential tissue ingrowth and entrapment.

In some embodiments, the tissue interface 120 may comprise more than one biopolymer layer, for example, two or three distinct biopolymer layers. Thus, the tissue interface 120 can be considered multi-layered. For example, a second or additional biopolymer layer 515 may be included in the tissue interface 120 as shown in FIG. 5C. In the example of FIG. 5C the second or additional biopolymer layer 515 (also referred to as an intermediate biopolymer) is interposed between the manifold 505 and the first or base biopolymer layer 510.

In some embodiments, the second or additional biopolymer layer 515 can be constructed with differential mechanical properties (e.g. different compressibility, stiffness, porosity, etc.) such that the second or additional biopolymer layer 515 collapses more quickly under negative pressure than the first or base biopolymer layer 510, resulting in limited exposed edges of the manifold 505 as shown in the example of FIG. 5C.

Thus, in some embodiments, the second or additional biopolymer layer 515 may have a greater dry state compressibility index value than either or both of the manifold 505 and the first or base biopolymer layer 510. For example, the dry state compressibility index value of the second biopolymer layer 515 may be 5%, 25% or even 50% greater than the dry state compressibility index value of the first biopolymer layer 510. In some embodiments, the second or additional biopolymer layer 515 has a dry state compressibility index value in the range of zero to 50% and a hydrated state compressibility index value in the range of 80%-100%. The second or additional biopolymer layer 515 may comprise any of the biopolymer materials listed above, for example, a biological material selected from the group consisting of heparin, collagen, gelatin, hyaluronic acid, chitosan, cellulose, a cellulose derivative, alginate, fibrin, silk, carrageenan, chondroitin sulfate, agarose, keratin, dextran, keratan sulfate, heparan sulfate, fibronectin, laminin, and a combination thereof.

In addition to dressings and therapy systems comprising a tissues interface 120 (or a wound insert), also provided herein are methods to make and customize a tissue interface 120.

In some embodiments, methods of making a dressing comprising a tissue interface 120 (or wound insert) may comprise contacting at least a portion of the manifold 505 with a biopolymer slurry in aqueous base; and freeze drying the manifold 505 and the biopolymer slurry to form the biopolymer layer 510.

In some embodiments, a biopolymer slurry can be prepared by forming a solution of biopolymer materials as described herein with an aqueous base, such as a 0.05M acetic acid solution. For example, in some embodiments 0.1% to 5%, preferably 1.25% to 3%, of collagen powder can be mixed with a 0.05M acetic acid solution, or water, or a weak acid or base to form a slurry, and 0.1% to 5%, preferably 1.25% to 3%, of cellulose, such as ORC, can be added to the slurry and mixed.

In some embodiments, the manifold 505 can be brought into contact with the biopolymer slurry, and optionally, depressed into the biopolymer slurry. The combination of manifold 505 and biopolymer slurry can then be frozen at a temperature of about −70° C. for a minimum of 30 minutes, and preferably in the range of about 12 to 24 hours. Once frozen the combination of the manifold 505 and the biopolymer slurry can be freeze dried to create the manifold 505 with the biopolymer layer 510 as a freeze dried sponge (which can also be referred to as a layer or sheet). Multiple tissue interfaces can be made from the same cast sheet, which can be cut out after freeze drying.

In some embodiments, the biopolymer layer 510 can be removably attached to the manifold 505.

Additionally or alternatively, methods of making a dressing comprising a tissue interface 120 (or a wound insert) may comprise preparing and freeze drying a biopolymer slurry as described above to form the biopolymer layer 510 and then contacting at least a portion of the manifold 505 with the biopolymer layer 510.

In some embodiments, a series of text or symbols can be printed post-fabrication on the biopolymer layer 510. The text or symbols may be used to guide an end user about tissue interface 120 or wound insert placement direction in a wound bed.

In further embodiments, the manifold 505 can also be manipulated to allow for customized compression, shape and size.

In some embodiments, the manifold 505 can be perforated. Perforating the manifold 505 can be performed before or after the biopolymer layer 510 is applied or contacted to the manifold 505, preferably before. Any suitable means can be used to perforate such as die cutting or slitting.

Figure 6:
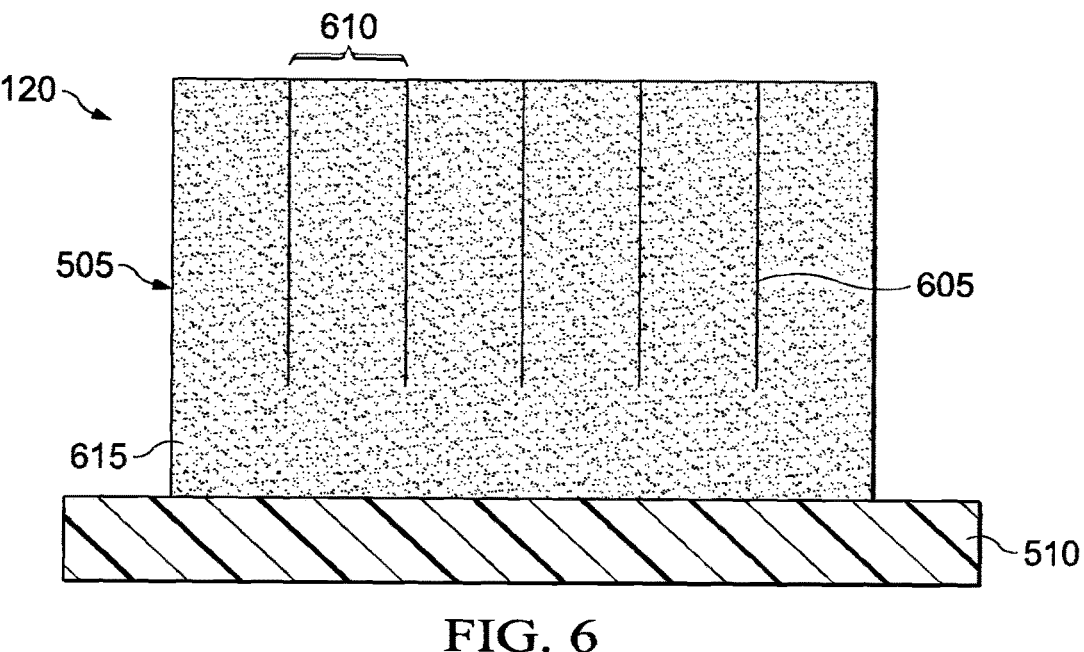
FIG. 6 is a side view of an example of a tissue interface illustrating additional details that may be associated with some embodiments of a manifold.
Figure 7:
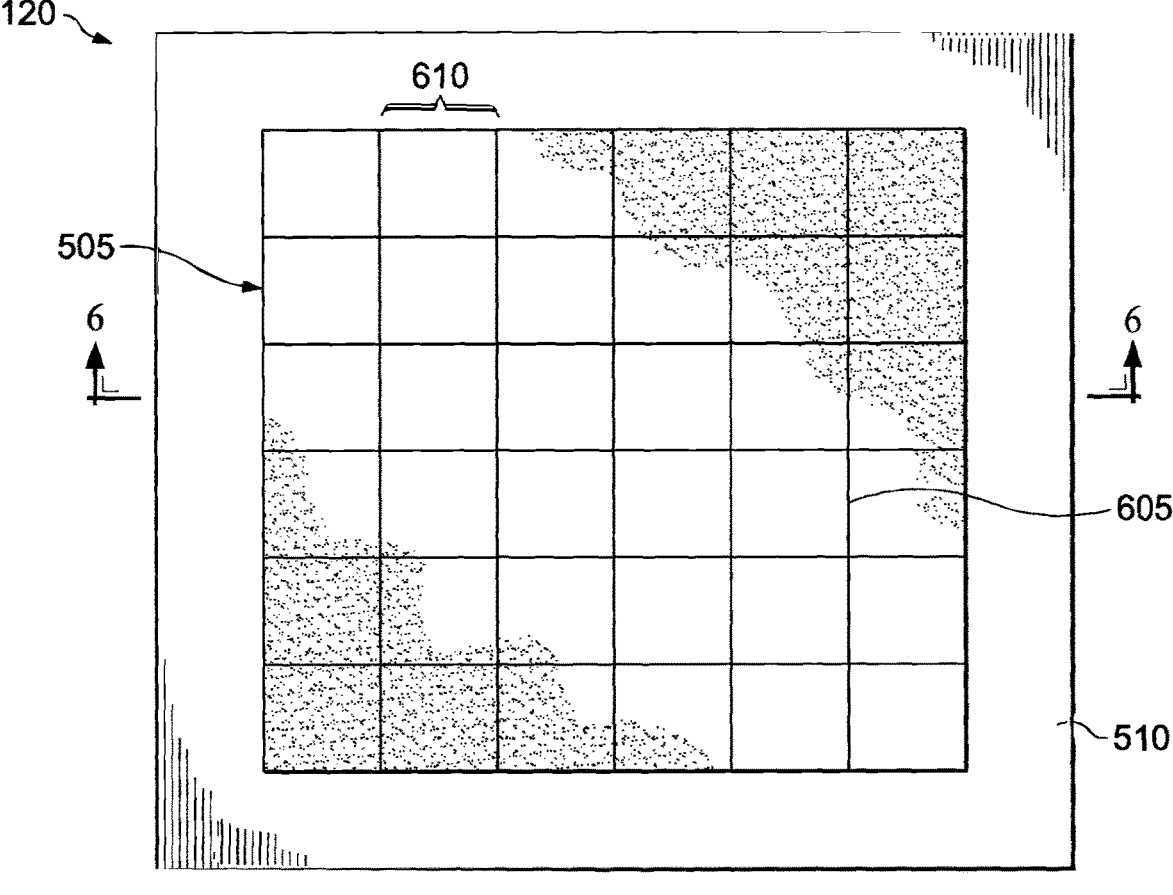
FIG. 7 is a top view of an example of a tissue interface illustrating additional details that may be associated with some embodiments of a manifold.

Additionally or alternatively, in some embodiments, the manifold 505 can have two or more partial cuts 605 and a base 615 as shown in the examples of FIG. 6 and FIG. 7. FIG. 6 is a side view of an example tissue interface 120 having a manifold 505 and a biopolymer layer 510, wherein the biopolymer layer 510 has a larger surface area than the manifold 505. The partial cuts 605 do not go all the way through the manifold 505, thus the base 615 of the manifold 505 is still intact. Partial cuts 605 allow the manifold 505 to collapse in on itself and to provide one or more removable parts or partial pillars 610. Thus, the manifold 505 can be said to have a partial pillar configuration. FIG. 7 is a top view of the example tissue interface 120 of FIG. 6. A partial pillar configuration allows an end user to remove one or more pillars 610 to increase the compression on one or more sides of tissue interface 120, and also to customize the size and shape of the tissue interface 120. Any suitable cutting means can be used for creating the partial pillars 610. For example, hot wire, laser cutting, die cutting with limited force, or wire jet may be used. Cutting the manifold 505 to create the partial pillars 610 can be performed before or after the biopolymer layer 510 is applied or contacted to the manifold 505, preferably before.

Figure 8:
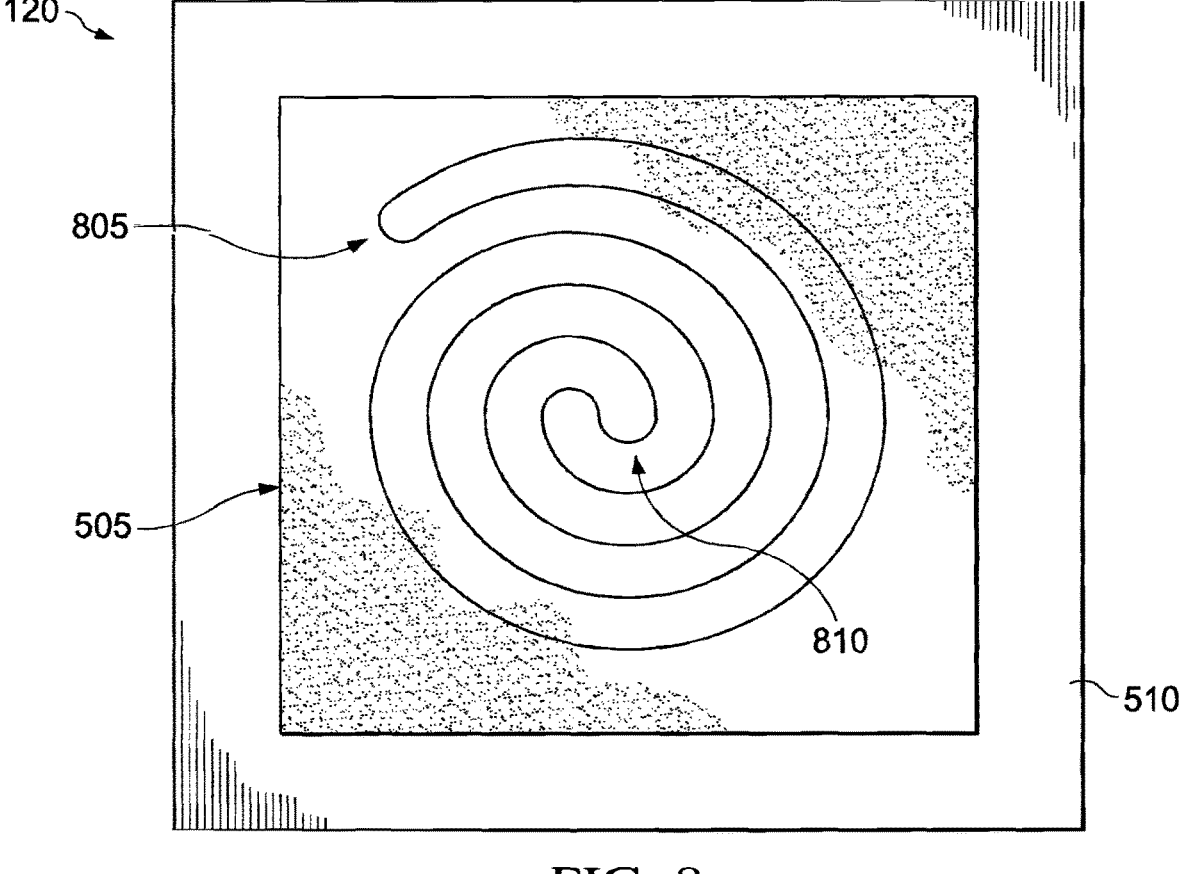
FIG. 8 is a top view of a tissue interface illustrating additional details that may be associated with some embodiments of a manifold.

Additionally or alternatively, in some embodiments the manifold 505 can be partially cut in a spiral shape (spiral cut) as shown in the top view of FIG. 8 to provide one or more removable parts to customize the size and shape of the manifold 505. One or more ends of the spiral cut can be removed from the manifold 505 to serve as a bridge landing pad. For example, spiral end 805 can be removed and placed on intact skin adjacent a wound. A dressing interface, such as a pad for receiving pressure (e.g. a SENSAT.R.A.C.™ Pad available from Kinetic Concepts, Inc. of San Antonio, Texas) can be applied to spiral end 805. Pressure can then be applied outside the wound to create a vacuum in the wound. This can be advantageous when, for example, a wound is at or near a nerve so as not to apply pressure on the nerve or when a wound is in a challenging location and a dressing cannot easily be placed over the wound location. Additionally or alternatively, spiral end 805 can be placed in a second wound and serve as a bridge to apply pressure to one or more wounds. Additionally or alternatively, spiral end 810 can also act as a bridge or bridge landing pad in a similar manner.

The systems, apparatuses, and methods described herein may provide significant advantages. For example, manifolding negative pressure through a porous dressing construct, such as the tissue interface 120, has been shown to stimulate granulation tissue formation. The construction and composition of the porous dressing construct can have an impact upon the clinical regimen. In the case of open cell foams, particularly those manufactured from materials that are not intended to permanently reside within the body such as polyurethane, the granulation tissue can grow into the dressing construct and entrap portions of the dressing within the newly formed tissue. In some embodiments, the tissue interface 120 described herein can reduce or prevent tissue ingrowth from the bottom and edges of a wound, which can improve both the wound healing process and patient comfort.

EXAMPLES

Example 1—Prototype Preparation

Collagen powder (Bovine dermis collagen source) was combined with an acetic acid solution (0.05M concentration) in a table top blender (2.2% w/v) and blended to disperse the collagen material within the solution. The dispersed collagen was allowed to swell within the blender and form a slurry. Once swelled oxidized regenerated cellulose powder (powdered Surgicel® from Ethicon) was added (1.8% w/v) to the collagen slurry. The resulting slurry mixture was blended to incorporate the oxidized regenerated cellulose powder. This slurry (4% w/v solids content) was then transferred to a new container and degassed to remove any pockets of trapped air through exposure to a vacuum. Once degassed the material was slowly poured into square petri trays (10×10 cm) with 62 g material added to each tray. A section of open cell hydrophobic polyurethane foam with an area of 10×10 cm (varying thickness depending on need) was placed onto the slurry mixture ensuring level/even contact between the two materials without air pockets. The process of application to the slurry mixture is sufficient to achieve a level of slurry integration into the foam material. There is no need to depress the foam material (unless greater integration between the materials is required). The resulting combination material is then frozen in a −70° C. freezer to generate a polyurethane foam material with a frozen biopolymer sheet at the interface. Once frozen this material is then freeze dried to generate a polyurethane foam material with attached freeze dried sponge of collagen and oxidized regenerated cellulose (~4 mm in thickness).

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, the controller 130 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for use in negative pressure wound therapy comprising:
   a manifold having a wound facing side, a non-wound facing side opposite the wound facing side, and outer edges between the wound facing and non-wound facing sides; and
   a first biopolymer layer coupled to the manifold;
   wherein the manifold has a compressibility index value greater than a dry state compressibility index value of the first biopolymer layer, and less than a hydrated state compressibility index value of the first biopolymer layer.

2. The dressing of claim 1, wherein the first biopolymer layer is configured to be in contact with the wound facing side and at least a portion of the outer edges of the manifold, and further configured to reduce or prevent the ingrowth of tissue into said portion of the outer edges during wound therapy.

3. The dressing of claim 1, wherein the first biopolymer layer is configured to contact said portion of the outer edges only during wound therapy, such as negative pressure wound therapy.

4. The dressing of claim 1, wherein the first biopolymer layer is separable from the manifold.

5. The dressing of claim 1, wherein the compressibility index value of the manifold is 10 to 50.

6. The dressing of claim 1, wherein the dry state compressibility index value of the first biopolymer layer is zero to 35 and the hydrated state compressibility index value of the first biopolymer layer is 65 to 90.

7. The dressing of claim 1, wherein the first biopolymer layer comprises a biological material selected from the group consisting of heparin, collagen, gelatin, hyaluronic acid, chitosan, cellulose, a cellulose derivative, alginate, fibrin, silk, carrageenan, chondroitin sulfate, agarose, keratin, dextran, keratan sulfate, heparan sulfate, fibronectin, laminin, and a combination thereof.

8. The dressing of claim 1, wherein the first biopolymer layer comprises a synthetic polymer selected from the group consisting of polycaprolactone, polylactic acid, polyglycolic acid, polydioxanone, poly(lactic-co-glycolic acid), and polyhydroxybutyrate, polyhydroxyvalerate and a combination thereof.

9. The dressing of claim 1, wherein the first biopolymer layer comprises collagen; and also comprises oxidized non-regenerated cellulose and/or oxidized regenerated cellulose.

10. The dressing of claim 1, wherein the first biopolymer layer comprises an antimicrobial agent.

11. The dressing of claim 1, wherein the first biopolymer layer is perforated and/or is printed on with text and/or symbols.

12. The dressing of claim 1, wherein the first biopolymer layer has a thickness of 0.1 cm to 5 cm.

13. The dressing of claim 1, wherein the first biopolymer layer has a density 0.01 g/cm3 to 0.06 g/cm3.

14. The dressing of claim 1, further comprising a second biopolymer layer, wherein the second biopolymer layer is interposed between the manifold and the first biopolymer layer.

15. The dressing of claim 14, wherein the second biopolymer layer has a dry state compressibility index value greater than the dry state compressibility index value of the first biopolymer layer.

16. The dressing of claim 1, wherein the manifold comprises silicone, polyvinyl alcohol, a combination thereof, or foam.

17. The dressing of claim 1, wherein the manifold has a thickness of 0.5 cm to 8 cm.

18. The dressing of claim 1, wherein an area of overlap between the manifold and the first biopolymer layer is 0.01 cm to 5 cm.

19. The dressing of claim 1, wherein the manifold and the first biopolymer layer together have a trapezoidal cross-section having an inclined angle of 20 to 85 degrees.

20. The dressing of claim 1, wherein the manifold is perforated or has one or more partial cuts.

\* \* \* \* \*